(12) United States Patent
Suslian et al.

(10) Patent No.: US 10,278,800 B2
(45) Date of Patent: *May 7, 2019

(54) METHOD AND DEVICE FOR TREATING URINARY INCONTINENCE

(71) Applicant: COLOPLAST A/S, Humlebaek (DK)

(72) Inventors: Patrice Suslian, Gordes (FR); Emmanuel Delorme, Chalon sur Saone (FR)

(73) Assignee: Coloplast A/S, Humlebaek (DK)

( * ) Notice: Subject to any disclaimer, the term of this patent is extended or adjusted under 35 U.S.C. 154(b) by 516 days.

This patent is subject to a terminal disclaimer.

(21) Appl. No.: 14/309,620

(22) Filed: Jun. 19, 2014

(65) Prior Publication Data

US 2014/0303431 A1 Oct. 9, 2014

Related U.S. Application Data

(60) Continuation of application No. 13/326,334, filed on Dec. 15, 2011, now Pat. No. 8,920,304, which is a (Continued)

(30) Foreign Application Priority Data

Jul. 5, 2000 (FR) ..................................... 00 08706

(51) Int. Cl.
*A61F 2/02* (2006.01)
*A61F 2/00* (2006.01)
*A61B 17/00* (2006.01)

(52) U.S. Cl.
CPC .. *A61F 2/0045* (2013.01); *A61B 2017/00805* (2013.01); *A61F 2/02* (2013.01); *A61F 2002/009* (2013.01)

(58) Field of Classification Search
CPC ...... A61F 2/0031; A61F 2/0036; A61F 2/045; A61F 2002/009
(Continued)

(56) References Cited

U.S. PATENT DOCUMENTS 2,738,790 A 3/1956 Todt, Sr. et al.
3,054,406 A 9/1962 Usher
(Continued)

FOREIGN PATENT DOCUMENTS

DE 2305815 A1 8/1974
DE 4220283 A1 12/1993
(Continued)

OTHER PUBLICATIONS

Abdel-fattah, Mohamed et al. Evaluation of transobturator tapes (E-TOT) study: randomised prospective single-blinded study comparing inside-out vs. outside-in transobturator tapes in management of urodynamic stress incontinence: Short term outcomes, European Journal of Obstetrics & Gynecology and Reproductive Biology (2009).
(Continued)

*Primary Examiner* — John P Lacyk
(74) *Attorney, Agent, or Firm* — Coloplast Corp., Coloplast A/S; Nick Baumann

(57) ABSTRACT

A method for treating urinary incontinence includes making a vaginal incision in a patient, and positioning a tape under the urethra through the incision such that one portion of the tape extends from under the urethra and diverts away from the bladder and other vital organs. In one embodiment, once positioned within the patient, the tape adopts a V-shape and provides support for the urethra without altering the position of the urethra.

18 Claims, 2 Drawing Sheets

Related U.S. Application Data continuation of application No. 12/547,499, filed on Aug. 26, 2009, now Pat. No. 8,469,875, which is a continuation of application No. 11/040,698, filed on Jan. 21, 2005, now Pat. No. 7,621,864, which is a continuation of application No. 10/455,465, filed on Jun. 4, 2003, now abandoned, which is a division of application No. 10/092,069, filed on Mar. 5, 2002, now Pat. No. 6,638,211, which is a continuation of application No. PCT/FR01/02120, filed on Jul. 3, 2001.

(58) Field of Classification Search
USPC .......... 600/29–32, 37; 128/DIG. 25; 606/141
See application file for complete search history.

(56) References Cited

U.S. PATENT DOCUMENTS

| | | |
|---|---|---|
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Winkle, Jr. |
| 3,472,232 A | 10/1969 | Pendleton |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,888,975 A | 6/1975 | Ramwell |
| 3,911,911 A | 10/1975 | Scommegna |
| 3,913,573 A | 10/1975 | Gutnick |
| 3,916,899 A | 11/1975 | Theeuwes et al. |
| 3,924,633 A | 12/1975 | Cook et al. |
| 3,993,058 A | 11/1976 | Hoff |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,233,968 A | 11/1980 | Shaw, Jr. |
| 4,235,238 A | 11/1980 | Ogiu et al. |
| 4,246,660 A | 1/1981 | Wevers |
| 4,441,497 A | 4/1984 | Paudler |
| 4,444,933 A | 4/1984 | Columbus et al. |
| 4,509,516 A | 4/1985 | Richmond |
| 4,632,100 A | 12/1986 | Somers |
| 4,633,873 A | 1/1987 | Dumican et al. |
| 4,646,731 A | 3/1987 | Brower |
| 4,655,221 A | 4/1987 | Devereux |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,938,760 A | 7/1990 | Burton et al. |
| 5,013,292 A | 5/1991 | Lemay |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,149,329 A | 9/1992 | Richardson |
| 5,188,636 A | 2/1993 | Fedotov |
| 5,207,694 A | 5/1993 | Broome |
| 5,209,756 A | 5/1993 | Seedhorn et al. |
| 5,250,033 A | 10/1993 | Evans et al. |
| 5,256,133 A | 10/1993 | Spitz |
| 5,259,835 A | 11/1993 | Clark et al. |
| 5,281,237 A | 1/1994 | Gimpelson |
| 5,328,077 A | 7/1994 | Lou |
| 5,336,239 A | 8/1994 | Gimpelson |
| 5,337,736 A | 8/1994 | Reddy |
| 5,342,376 A | 8/1994 | Ruff |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,434,146 A | 7/1995 | Labrie et al. |
| 5,439,467 A | 8/1995 | Benderev et al. |
| 5,456,711 A | 10/1995 | Hudson |
| 5,486,197 A | 1/1996 | Le et al. |
| 5,507,754 A | 4/1996 | Green et al. |
| 5,507,796 A | 4/1996 | Hasson |
| 5,520,700 A | 5/1996 | Beyar et al. |
| 5,522,896 A | 6/1996 | Prescott |
| 5,544,664 A | 8/1996 | Benderev et al. |
| 5,549,619 A | 8/1996 | Peters et al. |
| 5,562,685 A | 10/1996 | Mollenauer et al. |
| 5,562,689 A | 10/1996 | Green et al. |
| 5,569,273 A | 10/1996 | Titone et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,645,568 A | 7/1997 | Chervitz et al. |
| 5,647,836 A | 7/1997 | Blake, III et al. |
| 5,669,935 A | 9/1997 | Rosenman et al. |
| 5,683,349 A | 11/1997 | Makower et al. |
| 5,695,525 A | 12/1997 | Mulhauser et al. |
| 5,697,931 A | 12/1997 | Thompson |
| 5,697,978 A | 12/1997 | Sgro |
| 5,720,766 A | 2/1998 | Zang et al. |
| 5,749,884 A | 5/1998 | Benderev et al. |
| 5,766,221 A | 6/1998 | Benderev et al. |
| 5,807,403 A | 9/1998 | Beyar |
| 5,816,258 A | 10/1998 | Jervis |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,851,229 A | 12/1998 | Lentz et al. |
| 5,860,425 A | 1/1999 | Benderev et al. |
| 5,899,909 A | 5/1999 | Claren et al. |
| 5,904,692 A | 5/1999 | Steckel et al. |
| 5,919,232 A | 7/1999 | Chaffringeon et al. |
| 5,922,026 A | 7/1999 | Chin |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Boyar et al. |
| 5,988,171 A | 11/1999 | Sohn et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,039,686 A | 3/2000 | Kovac |
| 6,042,534 A * | 3/2000 | Gellman ............... A61F 2/0045 600/30 |
| 6,042,536 A | 3/2000 | Tihon et al. |
| 6,042,583 A | 3/2000 | Thompson et al. |
| 6,048,306 A | 4/2000 | Spielberg |
| 6,048,351 A | 4/2000 | Gordon et al. |
| 6,050,937 A | 4/2000 | Benderey |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,090,116 A | 7/2000 | D'Aversa et al. |
| 6,106,545 A | 8/2000 | Egan |
| 6,110,101 A | 8/2000 | Tihon et al. |
| 6,117,067 A | 9/2000 | Gil Vernet |
| 6,159,207 A | 12/2000 | Yoon |
| 6,162,962 A | 12/2000 | Hinsch et al. |
| 6,168,611 B1 | 1/2001 | Rizvi |
| 6,190,401 B1 | 2/2001 | Green et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,231,496 B1 | 5/2001 | Wilk et al. |

(56) References Cited

U.S. PATENT DOCUMENTS

| | | |
|---|---|---|
| 6,245,082 B1 | 6/2001 | Gellman et al. |
| 6,264,676 B1 | 7/2001 | Gellman et al. |
| 6,267,772 B1 | 7/2001 | Mulhauser et al. |
| 6,273,852 B1 | 8/2001 | Lehe et al. |
| 6,287,316 B1 | 9/2001 | Agarwal et al. |
| 6,292,700 B1 | 9/2001 | Morrison et al. |
| 6,302,840 B1 | 10/2001 | Benderev |
| 6,306,079 B1 | 10/2001 | Trabucco |
| 6,319,264 B1 | 11/2001 | Tormala et al. |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van der Burg et al. |
| 6,355,065 B1 | 3/2002 | Gabbay |
| 6,382,214 B1 | 5/2002 | Raz et al. |
| 6,387,041 B1 | 5/2002 | Harari et al. |
| 6,406,423 B1 * | 6/2002 | Scetbon ............ A61B 17/0469 128/898 |
| 6,406,480 B1 | 6/2002 | Beyar et al. |
| 6,408,656 B1 | 6/2002 | Ory et al. |
| 6,418,930 B1 | 7/2002 | Fowler |
| 6,443,964 B1 | 9/2002 | Ory et al. |
| 6,461,332 B1 | 10/2002 | Mosel et al. |
| 6,475,139 B1 | 11/2002 | Miller |
| 6,478,727 B2 | 11/2002 | Scetbon |
| 6,478,791 B1 | 11/2002 | Carter et al. |
| 6,482,214 B1 | 11/2002 | Sidor, Jr. et al. |
| 6,491,703 B1 | 12/2002 | Ulmsten |
| 6,494,887 B1 | 12/2002 | Kaladelfos |
| 6,494,906 B1 | 12/2002 | Owens |
| 6,502,578 B2 | 1/2003 | Raz et al. |
| 6,506,190 B1 | 1/2003 | Walshe |
| 6,527,802 B1 | 3/2003 | Mayer |
| 6,530,943 B1 | 3/2003 | Hoepffner et al. |
| 6,544,273 B1 | 4/2003 | Harari et al. |
| 6,575,897 B1 | 6/2003 | Ory et al. |
| 6,575,998 B2 | 6/2003 | Beyar |
| 6,582,443 B2 | 6/2003 | Cabak et al. |
| 6,592,515 B2 | 7/2003 | Thierfelder et al. |
| 6,596,001 B2 | 7/2003 | Stormby et al. |
| 6,599,235 B2 | 7/2003 | Kovac |
| 6,599,318 B1 | 7/2003 | Gabbay |
| 6,599,323 B2 | 7/2003 | Melican et al. |
| 6,612,977 B2 | 9/2003 | Staskin et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,652,450 B2 | 11/2003 | Neisz et al. |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,679,896 B2 | 1/2004 | Gellman et al. |
| 6,689,047 B2 | 2/2004 | Gellman |
| 6,691,711 B2 | 2/2004 | Raz et al. |
| 6,695,855 B1 | 2/2004 | Gaston |
| 6,702,827 B1 | 3/2004 | Lund et al. |
| 6,737,371 B1 | 5/2004 | Planck et al. |
| 6,755,781 B2 | 6/2004 | Getman |
| 6,786,861 B1 | 9/2004 | Pretorius |
| 6,830,052 B2 | 12/2004 | Carter et al. |
| 6,860,887 B1 | 3/2005 | Frankie |
| 6,884,212 B2 | 4/2005 | Thierfelder et al. |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,960,160 B2 | 11/2005 | Browning |
| 7,025,063 B2 | 4/2006 | Snitkin |
| 7,070,556 B2 | 7/2006 | Anderson et al. |
| 7,070,558 B2 | 7/2006 | Gellman et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,140,956 B1 | 11/2006 | Korovin et al. |
| 7,156,858 B2 | 1/2007 | Schuldt-Hempe et al. |
| 7,204,802 B2 | 4/2007 | De Leval |
| 7,229,404 B2 | 6/2007 | Bouffier |
| 7,288,063 B2 | 10/2007 | Petros et al. |
| 7,290,410 B2 | 11/2007 | Meneghin et al. |
| 7,297,102 B2 | 11/2007 | Smith et al. |
| 7,326,213 B2 | 2/2008 | Benderev et al. |
| 7,347,812 B2 | 3/2008 | Mellier |
| 7,387,634 B2 | 6/2008 | Benderev |
| 7,395,822 B1 | 7/2008 | Burton et al. |
| 7,410,460 B2 | 8/2008 | Benderev |
| 7,500,945 B2 | 3/2009 | Cox et al. |
| 7,517,313 B2 | 4/2009 | Thierfelder et al. |
| 7,527,633 B2 | 5/2009 | Rioux |
| 7,559,885 B2 | 7/2009 | Merade et al. |
| 7,594,921 B2 | 9/2009 | Browning |
| 7,601,118 B2 | 10/2009 | Smith et al. |
| 7,611,454 B2 | 11/2009 | De Leval |
| 7,614,258 B2 | 11/2009 | Cherok et al. |
| 7,621,864 B2 | 11/2009 | Suslian et al. |
| 7,628,156 B2 | 12/2009 | Astani et al. |
| 7,673,631 B2 | 3/2010 | Astani et al. |
| 7,686,760 B2 | 3/2010 | Anderson et al. |
| 7,691,050 B2 | 4/2010 | Gellman et al. |
| 7,713,188 B2 | 5/2010 | Bouffier |
| 7,722,528 B2 | 5/2010 | Arnal et al. |
| 7,740,576 B2 | 6/2010 | Hodroff et al. |
| 7,766,926 B2 | 8/2010 | Bosley, Jr. et al. |
| 7,789,821 B2 | 9/2010 | Browning |
| 7,794,385 B2 | 9/2010 | Rosenblatt |
| 7,815,662 B2 | 10/2010 | Spivey et al. |
| 7,927,342 B2 | 4/2011 | Rioux |
| 7,975,698 B2 | 7/2011 | Browning |
| 7,981,022 B2 | 7/2011 | Gellman et al. |
| 8,007,430 B2 | 8/2011 | Browning |
| 8,016,741 B2 | 9/2011 | Weiser et al. |
| 8,016,743 B2 | 9/2011 | Maroto |
| 8,047,983 B2 | 11/2011 | Browning |
| 8,092,366 B2 | 1/2012 | Evans |
| 8,118,727 B2 | 2/2012 | Browning |
| 8,118,728 B2 | 2/2012 | Browning |
| 8,123,673 B2 | 2/2012 | Browning |
| 8,128,554 B2 | 3/2012 | Browning |
| 8,162,818 B2 | 4/2012 | Browning |
| 8,167,785 B2 | 5/2012 | Browning |
| 8,182,412 B2 | 5/2012 | Browning |
| 8,182,413 B2 | 5/2012 | Browning |
| 8,215,310 B2 | 7/2012 | Browning |
| 8,273,011 B2 | 9/2012 | Browning |
| 8,449,450 B2 | 5/2013 | Browning |
| 8,454,492 B2 | 6/2013 | Browning |
| 8,469,875 B2 | 6/2013 | Suslian et al. |
| 8,469,877 B2 | 6/2013 | Browning |
| 8,512,223 B2 | 8/2013 | Browning |
| 8,574,148 B2 | 11/2013 | Browning et al. |
| 8,668,635 B2 | 3/2014 | Browning |
| 8,920,304 B2 * | 12/2014 | Suslian ................ A61F 2/0045 600/30 |
| 2001/0000533 A1 | 4/2001 | Kovac |
| 2001/0018549 A1 | 8/2001 | Scetbon |
| 2001/0039423 A1 | 11/2001 | Skiba et al. |
| 2001/0049467 A1 | 12/2001 | Lehe et al. |
| 2001/0049538 A1 | 12/2001 | Trabucco |
| 2001/0051815 A1 | 12/2001 | Esplin |
| 2001/0053916 A1 | 12/2001 | Rioux |
| 2002/0005204 A1 | 1/2002 | Benderev et al. |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0042658 A1 | 4/2002 | Tyagi |
| 2002/0049503 A1 | 4/2002 | Milbocker |
| 2002/0052612 A1 | 5/2002 | Schmitt et al. |
| 2002/0052654 A1 | 5/2002 | Darois et al. |
| 2002/0055748 A1 | 5/2002 | Gellman et al. |
| 2002/0058959 A1 | 5/2002 | Gellman et al. |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |

(56) References Cited

U.S. PATENT DOCUMENTS

| | | |
|---|---|---|
| 2002/0078964 A1 | 6/2002 | Kovac et al. |
| 2002/0082619 A1 | 6/2002 | Cabak et al. |
| 2002/0083949 A1 | 7/2002 | James |
| 2002/0091298 A1 | 7/2002 | Landgrebe |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslian et al. |
| 2002/0103542 A1 | 8/2002 | Bilbo |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0119177 A1 | 8/2002 | Bowman et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz et al. |
| 2002/0183588 A1 | 12/2002 | Fierro |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0069469 A1 | 4/2003 | Li |
| 2003/0078468 A1 | 4/2003 | Skiba et al. |
| 2003/0100954 A1 | 5/2003 | Schuldt Hempe et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0176875 A1 | 9/2003 | Anderson et al. |
| 2003/0191360 A1 | 10/2003 | Browning |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0029478 A1 | 2/2004 | Planck et al. |
| 2004/0034373 A1 | 2/2004 | Schuldt-Hempe et al. |
| 2004/0039453 A1 | 2/2004 | Anderson et al. |
| 2004/0059356 A1 | 3/2004 | Gingras |
| 2004/0097974 A1 | 5/2004 | De Leval |
| 2004/0106847 A1 | 7/2004 | Benderev |
| 2004/0133217 A1* | 7/2004 | Watschke ......... A61B 17/06109 606/148 |
| 2004/0144395 A1 | 7/2004 | Evans et al. |
| 2004/0172048 A1 | 9/2004 | Browning |
| 2004/0231678 A1 | 11/2004 | Fierro |
| 2004/0243166 A1 | 12/2004 | Odermatt et al. |
| 2004/0249240 A1 | 12/2004 | Goldmann et al. |
| 2004/0249373 A1 | 12/2004 | Gronemeyer et al. |
| 2004/0249397 A1 | 12/2004 | Delorme et al. |
| 2004/0249473 A1 | 12/2004 | Delorme et al. |
| 2005/0000524 A1 | 1/2005 | Cancel et al. |
| 2005/0004576 A1 | 1/2005 | Benderev |
| 2005/0080317 A1 | 4/2005 | Merade |
| 2005/0107805 A1 | 5/2005 | Bouffier et al. |
| 2005/0131274 A1 | 6/2005 | Suslian et al. |
| 2005/0240076 A1 | 10/2005 | Neisz et al. |
| 2005/0277806 A1 | 12/2005 | Cristalli |
| 2005/0278037 A1 | 12/2005 | Delorme et al. |
| 2005/0283040 A1 | 12/2005 | Greenhalgh |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058578 A1 | 3/2006 | Browning |
| 2006/0089524 A1 | 4/2006 | Chu |
| 2006/0089525 A1 | 4/2006 | Mamo et al. |
| 2006/0130848 A1 | 6/2006 | Carey |
| 2006/0173468 A1* | 8/2006 | Simmon ......... A61B 17/06109 606/113 |
| 2006/0205995 A1 | 9/2006 | Browning |
| 2006/0264698 A1 | 11/2006 | Kondonis et al. |
| 2007/0015953 A1 | 1/2007 | MacLean |
| 2007/0020311 A1 | 1/2007 | Browning |
| 2007/0032695 A1 | 2/2007 | Weiser |
| 2007/0032881 A1 | 2/2007 | Browning |
| 2007/0059199 A1 | 3/2007 | Labuschagne |
| 2007/0149555 A1 | 6/2007 | Kase et al. |
| 2007/0219606 A1 | 9/2007 | Moreci et al. |
| 2008/0021263 A1 | 1/2008 | Escude et al. |
| 2008/0161837 A1 | 7/2008 | Toso et al. |
| 2008/0161850 A1 | 7/2008 | Weisenburgh et al. |
| 2008/0167518 A1 | 7/2008 | Burton et al. |
| 2008/0196729 A1 | 8/2008 | Browning |
| 2008/0200751 A1 | 8/2008 | Browning |
| 2009/0123522 A1 | 5/2009 | Browning |
| 2009/0137862 A1 | 5/2009 | Evans et al. |
| 2009/0171377 A1 | 7/2009 | Intoccia et al. |
| 2009/0221868 A1 | 9/2009 | Evans |
| 2009/0287229 A1 | 11/2009 | Ogdahl |
| 2010/0022822 A1 | 1/2010 | Walshe |
| 2010/0056856 A1 | 3/2010 | Suslian et al. |
| 2010/0063351 A1 | 3/2010 | Witzmann et al. |
| 2010/0113869 A1 | 5/2010 | Goldman |
| 2010/0130814 A1 | 5/2010 | Dubernard |
| 2010/0198002 A1 | 8/2010 | O'Donnell |
| 2010/0222794 A1 | 9/2010 | Browning |
| 2010/0222974 A1 | 9/2010 | Nakamura et al. |
| 2010/0256442 A1 | 10/2010 | Ogdahl et al. |
| 2010/0274074 A1 | 10/2010 | Khamis et al. |
| 2010/0280308 A1 | 11/2010 | Browning |
| 2010/0298630 A1 | 11/2010 | Wignall |
| 2011/0021868 A1 | 1/2011 | Browning |
| 2011/0034759 A1 | 2/2011 | Ogdahl et al. |
| 2011/0105833 A1 | 5/2011 | Gozzi et al. |
| 2011/0124954 A1 | 5/2011 | Ogdahl et al. |
| 2011/0124956 A1 | 5/2011 | Mujwid et al. |
| 2011/0201872 A1 | 8/2011 | Browning |
| 2011/0230705 A1 | 9/2011 | Browning |
| 2011/0230708 A1 | 9/2011 | Browning |
| 2011/0230709 A1 | 9/2011 | Browning |
| 2011/0237865 A1 | 9/2011 | Browning |
| 2011/0237866 A1 | 9/2011 | Browning |
| 2011/0237867 A1 | 9/2011 | Browning |
| 2011/0237868 A1 | 9/2011 | Browning |
| 2011/0237869 A1 | 9/2011 | Browning |
| 2011/0237870 A1 | 9/2011 | Browning |
| 2011/0237873 A1 | 9/2011 | Browning |
| 2011/0237874 A1 | 9/2011 | Browning |
| 2011/0237875 A1 | 9/2011 | Browning |
| 2011/0237876 A1 | 9/2011 | Browning |
| 2011/0237877 A1 | 9/2011 | Browning |
| 2011/0237878 A1 | 9/2011 | Browning |
| 2011/0237879 A1 | 9/2011 | Browning |
| 2011/0238095 A1 | 9/2011 | Browning |
| 2011/0245594 A1 | 10/2011 | Browning |
| 2011/0282136 A1 | 11/2011 | Browning |
| 2012/0083649 A1 | 4/2012 | Suslian et al. |
| 2012/0143000 A1 | 6/2012 | Browning |
| 2012/0149977 A1 | 6/2012 | Browning |
| 2012/0199133 A1 | 8/2012 | Browning |
| 2014/0039244 A1 | 2/2014 | Browning |
| 2014/0039247 A1 | 2/2014 | Browning |
| 2014/0039248 A1 | 2/2014 | Browning |
| 2014/0051917 A1 | 2/2014 | Browning |

FOREIGN PATENT DOCUMENTS

| | | |
|---|---|---|
| DE | 4304353 A1 | 4/1994 |
| DE | 10019604 C2 | 6/2002 |
| EP | 0009072 A1 | 4/1980 |
| EP | 0024781 B1 | 8/1984 |
| EP | 0024780 B1 | 10/1984 |
| EP | 0248544 B1 | 4/1991 |
| EP | 0139286 B1 | 8/1991 |
| EP | 0470308 A1 | 2/1992 |

(56) References Cited

FOREIGN PATENT DOCUMENTS

| | | |
|---|---|---|
| EP | 0557964 A1 | 9/1993 |
| EP | 0632999 A1 | 1/1995 |
| EP | 0650703 A1 | 5/1995 |
| EP | 0706778 A1 | 4/1996 |
| EP | 1093758 A1 | 4/2001 |
| EP | 0719527 B1 | 8/2001 |
| EP | 0643945 B1 | 3/2002 |
| EP | 1060714 B1 | 8/2006 |
| EP | 1274370 B1 | 9/2006 |
| EP | 1296614 B1 | 9/2006 |
| EP | 0797962 B2 | 9/2009 |
| FR | 1274370 A | 10/1961 |
| FR | 2712177 A1 | 5/1995 |
| FR | 2732582 A1 | 10/1997 |
| FR | 2735015 A1 | 2/1998 |
| FR | 2811218 E | 11/2000 |
| FR | 2787990 A1 | 4/2001 |
| GB | 0378288 A | 8/1932 |
| GB | 2353220 A | 2/2001 |
| RU | 2187251 C1 | 8/2002 |
| RU | 2196518 C2 | 1/2003 |
| SU | 1225547 A1 | 4/1986 |
| SU | 1342486 A1 | 10/1987 |
| SU | 1475607 A1 | 4/1989 |
| WO | WO1991000714 A1 | 1/1991 |
| WO | WO1993017635 A1 | 9/1993 |
| WO | WO1993019678 A2 | 10/1993 |
| WO | WO1995033454 A1 | 12/1995 |
| WO | WO1996003091 A1 | 2/1996 |
| WO | WO1996006567 A1 | 3/1996 |
| WO | WO1997013465 A1 | 4/1997 |
| WO | WO1997022310 A2 | 6/1997 |
| WO | WO1997043982 A1 | 11/1997 |
| WO | WO1998019606 A1 | 5/1998 |
| WO | WO1998035606 A2 | 8/1998 |
| WO | WO1998035616 A1 | 8/1998 |
| WO | WO1998035632 A1 | 8/1998 |
| WO | WO1998057590 A1 | 12/1998 |
| WO | WO1999016381 A1 | 4/1999 |
| WO | WO1999052450 A1 | 10/1999 |
| WO | WO1999059477 A1 | 11/1999 |
| WO | WO2000007520 A1 | 2/2000 |
| WO | WO2000013601 A1 | 3/2000 |
| WO | WO2000015141 A1 | 3/2000 |
| WO | WO2000018319 A1 | 4/2000 |
| WO | WO2000038784 A1 | 7/2000 |
| WO | WO2000057812 A1 | 10/2000 |
| WO | WO2000064370 A1 | 11/2000 |
| WO | WO2000074594 A1 | 12/2000 |
| WO | WO2000074613 A1 | 12/2000 |
| WO | WO2000074633 A2 | 12/2000 |
| WO | WO2001006951 A1 | 2/2001 |
| WO | WO2001026581 A1 | 4/2001 |
| WO | WO2001039670 A1 | 6/2001 |
| WO | WO2001045589 A1 | 6/2001 |
| WO | WO2001052729 A2 | 7/2001 |
| WO | WO2001056499 A1 | 8/2001 |
| WO | WO2001080773 A1 | 11/2001 |
| WO | WO2002002031 A1 | 1/2002 |
| WO | WO2002026108 A2 | 4/2002 |
| WO | WO2002028312 A1 | 4/2002 |
| WO | WO2002030293 A1 | 4/2002 |
| WO | WO2002032284 A2 | 4/2002 |
| WO | WO2002032346 A1 | 4/2002 |
| WO | WO2002034124 A2 | 5/2002 |
| WO | WO2002039890 A2 | 5/2002 |
| WO | WO2002060371 A1 | 8/2002 |
| WO | WO2002065921 A1 | 8/2002 |
| WO | WO2002065944 A1 | 8/2002 |
| WO | WO2002069781 A2 | 9/2002 |
| WO | WO2002071953 A2 | 9/2002 |
| WO | WO2002078548 A1 | 10/2002 |
| WO | WO2002078552 A1 | 10/2002 |
| WO | WO2002078568 A1 | 10/2002 |
| WO | WO2002078571 A2 | 10/2002 |
| WO | WO2002098340 A1 | 12/2002 |
| WO | WO2003002027 A1 | 1/2003 |
| WO | WO2003013392 A1 | 2/2003 |
| WO | WO2003057074 A2 | 7/2003 |
| WO | WO2003022260 B1 | 10/2003 |
| WO | WO2003086205 A2 | 10/2003 |
| WO | WO2003092546 A2 | 11/2003 |
| WO | WO2003094781 A1 | 11/2003 |
| WO | WO2004002370 A1 | 1/2004 |
| WO | WO2004002379 A1 | 1/2004 |
| WO | WO2004004600 A1 | 1/2004 |
| WO | WO2004012626 A1 | 2/2004 |
| WO | WO2004098461 A2 | 11/2004 |
| WO | WO2005018494 A1 | 3/2005 |
| WO | WO2005112842 A1 | 12/2005 |
| WO | WO2006015031 A2 | 2/2006 |
| WO | WO2006015042 A1 | 2/2006 |
| WO | WO2006136625 A1 | 12/2006 |
| WO | WO2007059199 A2 | 5/2007 |
| WO | WO2007149555 A2 | 12/2007 |
| WO | WO2008007086 A2 | 1/2008 |
| WO | WO2008018494 A1 | 2/2008 |

OTHER PUBLICATIONS

Aldridge, "Transplantation of Fascia for Relief of Urinary Stress Incontinence," Am. J. Obstet. Gynecol., 1942, 44:398-411.
Amended Answer and Counterclaim (Mar. 30, 2004) *American Medical Systems, Inc. v. Mentor Corporation*, Civ. No. 03-5759.
AMS's Reply to Mentor's Counterclaim (Apr. 5, 2004) *American MedicalSystems, Inc. v. Mentor Corporation*, Civ. No. 03-CV-5759.
Answer and Counterclaim (Mar. 2004) *American Medical Systems, Inc. v. Mentor Corporation*, Civ. No. 03-5759.
Answer and Counterclaim of American Medical Systems, Inc. (Mar. 11, 2004) *Mentor Corporation v. American Medical Systems, Inc.*, Civ. Case No. Apr. 1000 DWF/SRN.
Araki et al., "The Loop-Loosening Procedure for Urination Difficulties After Stamey Suspension of the Vesical Neck," J. Urol., 1990, 144:319-323.
Asmussen and Ulmsten, "Simultaneous Urethro-Cystometry with a New Technique," Scand. J. Urol. Nephrol., 1976, 10:7-11.
Beck and McCormick, "Treatment of Urinary Stress Incontinence with Anterior Colporrhaphy," Obstetrics and Gynecology, 1982, 59(3):271-274.
Benderev, "A Modified Percutaneous Outpatient Bladder Neck Suspension System," J. Urol., 1994, 152:2316-2320.
Benderev, "Anchor Fixation and Other Modifications of Endoscopic Bladder Neck Suspension," Urology, 1992, 40(5):409-418.
Bergman and Elia, "Three surgical procedures for genuine stress incontinence: Five-year follow-up of a prospective randomized study," Am. J. Obstet. Gynecol., 1995, 173:66-71.
Blaivas and Jacobs, "Pubovaginal Fascial Sling for the Treatment of Complicated Stress Urinary Incontinence," J. Urol., 1991, 145:1214-1218.
Blaivas and Salinas, "Type III Stress Urinary Incontinence: Importance of Proper Diagnosis and Treatment," American College of Surgeons Surgical Forum, 1984, 70.sup.th Annual Clinical Congress, San Francisco, CA, vol. XXXV, pp. 473-474.
Botros, Cystocele and Rectocele Repair: More Success With Mesh? Jun. 2006.
Bryans, "Marlex gauze hammock sling operation with Cooper's ligament attachment in the management of recurrent urinary stress incontinence," Am. J. Obstet, Gynecol., 1979, 133(3):292-294.
Burch, "Urethrovaginal fixation to Cooper's ligament for correction of stress incontinence, cystocele, and prolapse," Am. J. Obstet. Gynecol., 1961, 81(2):281-290.
Certified copy of priority document for GB Application No. 0025068.8, filed Oct. 12, 2000, 38 pages.
Certified copy of priority document for GB Application No. 0208359.0, filed Apr. 11, 2002, 50 pages.
Certified copy of priority document for GB Application No. 0411360.1, filed May 21, 2004, 31 pages.
Chen, Biologic Grafts and Synthetic Meshes in Pelvic Reconstructive Surgery, Jun. 2007.

(56) References Cited

OTHER PUBLICATIONS

Choe and Staskin, "Gore-Tex Patch Sling: 7 Years Later," Urology, 1999, 54:641-646.
Chopra et al., "Technique of Rectangular Fascial Sling,"' Female Urology, 1996, Raz (ed.), W.B. Saunders Company, Chapter 34, pp. 392-394.
Complaint and Jury Demand (Feb. 8, 2010), *Coloplast A/S v. Mpathy Medical Devices, Inc.*, Court File No. CV10-206.
Complaint for Declaratory Judgment (Oct. 28, 2003) *American Medical Systems, Inc. v. Mentor Corporation*.
Complaint for Patent Infringement (Feb. 20, 2004) *Mentor Corporation v. American Medical Systems, Inc.*
Complaint for Patent Infringement and Exhibits (Feb. 8, 2010) *Coloplast A/S, v. Generic Medical Devices, Inc.*, Court File No. CV10-227 BHS.
D. Elliott Declaration and Attachment 1 (Jan. 5, 2011) *Coloplast A/S, v. Generic Medical Devices, Inc.*, Court File No. CV 10-227 BHS.
Dargent, D. et al., Pose d'un ruban sous uretral oblique par voie obturatrice dans le traitement de L'incontinence urinary feminine [English "Insertion of a transobturator oblique suburethral sling in the treatment of female urinary incontinence"], Gynecol. Obstet. Ferril. 14, pp. 576-582 (2002) [including English translation at the beginning of document].
Das and Palmer, "Laparoscopic Colpo-Suspension," J. Urol., 1995, 154:1119-1121.
de Leval, J., "Novel Surgical Technique for the Treatment of Female Stress Urinary Continence: Transobturator Vaginal Tape Inside-Out," European Urology, 2003, 44:724-730.
DeBord, James R., (1998), "The Historical Development of Prosthetics in Hernia Surgery," Surgical Clinics of North America, 78(6): 973-1006.
Declaration of Dr. George D. Webster in Support of Generic Medical Devices, Inc.'s Briefing on Claim Construction and Exhibits for *Coloplast A/S, v. Generic Medical Devices, Inc.*, Court File No. CV 10-227 BHS, signed Jan. 5, 2011.
Declaration of Jeya Paul and Attachment 1 (Jan. 10, 2011) *Coloplast A/S, v. Generic Medical Devices, Inc.*, Court File No. CV 10-227 BHS.
Declaration of Marc Belloli in Support of GMD's Opening Claim Construction Brief and Exhibits A-J (Jan. 10, 2011) *Coloplast A/S v. Generic Medical Devices, Inc.*, Court File No. CV 10-227 BHS.
Decter, "Use of the Fascial Sling for Neurogenic Incontinence: Lessons Learned," J. Urol., 1993, 150:683-686.
Delmore, E. et al., La bandelette trans-obturatrice: Un procede mini-invasif pour traiter l'incontinence urinaire d'effort de la femme, Progres en Urologie, vol. 11, pp, 1306-1313 (2001) [including English translation at the beginning of document] .
deTayrac, et al. Prolapse repair by vaginal route using . . . Int. Urogynecol. J. (published online May 13, 2006).
Dwyer, Transvaginal repair of anterior and posterior compartment prolapse with Atrium polypropylene mesh, BJOG: An International Journal of Obstetrics & Gynaecology, Aug. 2004.
Enzelsberger et al., "Urodynamic and Radiologic Parameters Before and After Loop Surgery for Recurrent Urinary Stress Incontinence," Acta Obstet. Gynecol, Scand., 1990, 69:51-54.
Eriksen et al., "Long-Term Effectiveness of the Burch Colposuspension in Female Urinary Stress Incontinence," Acta Obstet. Gynecol. Scand., 1990, 69:45-50.
Falconer et al., "Clinical Outcome and Changes in Connective Tissue Metabolism After Intravaginal Slingplasty in Stress Incontinent Women," Int. Urogynecol. J., 1996, 7:133-137.
Falconer et al., "Influence of Different Sling Materials on Connective Tissue Metabolism in Stress Urinary Incontinent Women," Int. Urogynecol. J., 2001, (Suppl. 2):S19-S23.
Generic Medical Devices, Inc.'s Answer to Complaint and Counterclaims (Mar. 1, 2010) *Coloplast A/S, v. Generic Medical Devices, Inc.*, Court File No. CV10-227 BHS.
Generic Medical Devices, Inc.'s Non, Infringement and Invalidity Contentions and Accompanying Document Production (Aug. 9, 2010) *Coloplast A/S, v. Generic Medical Devices, Inc.*, Court File No. CV-I0-227 BHS.
Generic Medical Devices, Inc.'s Opening Claim Construction Brief (Jan. 10, 2011) *Coloplast A/S, v. Generic Medical Devices, Inc.*, Court File No. CV10-227 BHS.
Gilja et al., "A Modified Raz Bladder Neck Suspension Operation (Transvaginal Burch)," J. Urol., 1995, 153:1455-1457.
Gittes and Loughlin, "No-Incision Pubovaginal Suspension for Stress Incontinence," J. Urol,, 1987, 138:568-570.
Gruss, "The Obturator Bypass. Indications. Techniques. Outcomes," Chirurgie, 1971, 97:220-226.
Guida and Moore, "The Surgeon At Work. Obturator Bypass Technique," Surgery, Gynecology & Obstetrics, 1969, pp. 1307-1315.
Handa et al., "Banked Human Fascia Lata for the Suburethral Sling Procedure: A Preliminary Report:," Obstet, Gynecol., 1996, 88:1045-1049.
Hardiman, et al. Cystocele repair using polypropylene mesh. Br. J. Obstet. Gynaecol. 107: 825-26 (2000).
Henriksson and Ulmsten, "A urodynamic evaluation of the effects of abdominal urethrocystopexy and vaginal sling urethroplasty in women with stress incontinence," Am. J. Obstet. Gynecol., 1978, 131:77-82.
Hodgkinson and Kelly, "Urinary Stress Incontinence in the Female. III. Round-ligament technique for retropubic suspension of the urethra," Obstet. Gynecol., 1957, 10:493-499.
Hohenfellner and Petri, "Sling Procedures," Surgery of Female Incontinence, 2nd edition, SpringerVerlag, pp. 105-113, 1986.
Holschneider et al., "The Modified Pereyra Procedure in Recurrent Stress Urinary Incontinence: A 15-Year Review," Obstet. Gynecol., 1994, 83:573-578.
Horbach et al., "A Suburethral Sling Procedure with Polytetrafluoroethylene for the Treatment of Genuine Stress Incontinence in Patients with Low Urethral Closure Pressure," Obstet. Gynecol., 1988, 71:648-652.
Horbach, "Suburethral Sling Procedures," Urogynecology and Urodynamics—Theory and Practice, 1996, Williams & Wilkins, pp. 569-579.
Ingelman-Sundberg and Ulmsten, "Surgical Treatment of Female Urinary Stress Incontinence," Contr. Gynec. Obstet., 1983, 10:51-69.
International Preliminary Examination Report issued in PCT/GB01/04554, completed Nov. 22, 2002, 6 pages.
International Search Report and Written Opinion issued in PCT/GB2004/001390, dated Sep. 3, 2004, 12 pages.
International Search Report for PCT/GB2009/050174, dated Jun. 24, 2009.
International Search Report issued in PCT/GB01/04554, dated Jan. 29, 2002, 3 pages.
International Search Report issued in PCT/GB2007/002589, dated Jan. 22, 2008, 5 pages.
Jacquetin, Bernard, "2. Utilisation du "TVT" dans la chirurgie de l'incontinence urinaire feminine", J. Obstet. Biol. Reprod. 29: 242-47 (2000).
Jeffcoate, "The Results of the Aldridge Sling Operation for Stress Incontinence," The Journal of Obstetrics and Gynaecology of the British Empire, 1956, 63:36-39.
Jeter, "The Social Impact of Urinary incontinence," Female Urology, Raz (ed.), W. B. Saunders Company, 1996, Chapter 7, pp. 80-86.
Joint Claim Construction and Prehearing Statement Pursuant to Local Patent Rule 132 and Appendix A (Nov. 15, 2010) *Coioplast A/S, v. Generic Medical Devices, Inc.*, Court File No. CV10-227 BHS.
Karram and Bhatia, "Patch Procedure: Modified Transvaginal Fascia Lata Sling for Recurrent or Severe Stress Urinary Incontinence," Obstet Gynecol., 1990, 75:461-463.
Kerdiles et al., "Bypass via the Obturator Foramen in Reconstructive Arterial Surgery of the Lower Extremities," Ann. Chir. Thorac. Cardio-Vasc., 1974, 13(4):335-341.

(56) References Cited

OTHER PUBLICATIONS

Kerr and Staskin, "The Use of Artificial Material for Sling Surgery in the Treatment of Female Stress Urinary Incontinence," Female Urology, 1996, Raz (ed.), W.B. Saunders Company, Chapter 33, pp. 382-391.
Kersey, "The gauze hammock sling operation in the treatment of stress incontinence," Br. J. Obstet. Gynecol., 1983, 90:945-949.
Klinge et al., "Functional and Morphological Evaluation of a Low-Weight, Monofilament Polypropylene Mesh for Hernia Repair," Journal of Biomedical Material Research, Jan. 24, 2002, pp. 129-137.
Klinge, U. et al., "Influence of polyglactin-coating on functional and morphological parameters of polypropylene-mesh modifications for abnormal wall repair," Biomaterials 20 (1999), pp. 613-623.
Klinge, U. et al., "Modified Mesh for Hernia Repair that is Adapted to the Physiology of the Abdominal Wall," Eur J Surg 164:951-960 (1998).
Klinge, U, et al., "Pathophysiology of the abdominal wall," Der Chirurg, (1996),67: 229-233.
Klosterhalfen, B, et al., "Functional and morphological evaluation of different polypropylene-mesh modifications for abdominal wall repair," Biomaterials 19:2235-2246 (1998).
Klosterhalfen, B. et al., "Morphological correlation of the functional mechanics of the abdominal wall after mesh implantation," Langenbecks Arch Chir 382:87-94 (1997).
Klutke et al., "The Anatomy of Stress Incontinence: Magnetic Resonance Imaging of the Female Bladder Neck and Urethra," J. Urol., 1990, 143:563-566.
Klutke et al., "Transvaginal Badder Neck Suspension to Cooper's Ligament: A Modified Pereyra Procedure," Obstet. Gynecol., 1996, 88:294-297.
Korda et al., "Experience with Silastic Slings for Female Urinary Incontinence," Aust. Nz J. Obstet. Gynaecol., 1989, 29:150-154.
Kovac and Cruikshank, "Pubic Bone Suburethral Stabilization Sling for Recurrent Urinary Incontinence," Obstet. Gynecol., 1997, 89:624-627.
Kovac and Cruikshank, "Pubic bone suburethral stabilization sling: a long-term cure for SUI?" Contemporary OB/GYN, 1998, 43(2):51-72.
Kovac, "Follow-up of the Pubic Bone Suburethral Stabilization Sling Operation for Recurrent Urinary Incontinence (Kovac Procedure)," J. Pelvic Surgery, 1999, 5(3):156-160.
Lazarevski, M.B., Suburethral Duplication of the Vaginal Wall—An Original Operation for Urinary Stress Incontinence in Women, 6 Int'l Urogynecol. J. 73-79 (1995).
Leach et al., "Female Stress Urinary Incontinence Clinical Guidelines Panel Summary Report on Surgical Management of Female Stress Urinary Incontinence," J. Urol., 1997, 158:875-880.
Leach, "Bone Fixation Technique for Transvaginal Needle Suspension," Urology, 1988, 31(5):388-390.
Lichtenstein et al., "The Tension-Free Hernioplasty," Am. J. Surgery, 1989, 157:188-193.
Lipton, S. and Estrin, J., "A Biomechanical Study of the Aponeurotic Iguinal Hernia Repair," Journal of the American College of Surgeons, Jun. 1994, vol. 178, pp. 595-599.
Loughlin et al., "Review of an 8-Year Experience with Modifications of Endoscopic Suspension of the Bladder Neck for Female Stress Urinary Incontinence," J. Urol., 1990, 143:44-45.
Maher, Surgical Management of Anterior Vaginal Wall Prolapse: An Evidence Based Literature Review, 2006.
Mahoney and Whelan, "Use of Obturator Foramen in Iliofemoral Artery Grafting: Case Reports," Annals of Surgery, 1966. 163(2):215-220.
Marshall et al., "The Correction of Stress Incontinence by Simple Vesicourethral Suspension," J. Urol., 2002, 168:1326-1331.
McGuire and Gormley, "Abdominal Fascial Slings," Female Urology, 1996, Raz (ed.), W.B. Saunders Company, Chapter 31, pp. 369-375.
McGuire and Lytton, "Pubovaginal Sling Procedure for Stress Incontinence," J. Urol., 1978, 119:82-84.
McGuire et al., "Experience with Pubovaginal Slings for Urinary Incontinence at the University of Michigan," J. Urol., 1987, 138:525-526.
McGuire, "Abdominal Procedures for Stress Incontinence," Urologic Clinics of North America, 1985, 12(2):285-290.
McIndoe et al., "The Aldridge Sling Procedure in the Treatment of Urinary Stress Incontinence," Aust. Nz J. Obstet, Gynaecol., 1987, 27:238-239.
McKiel, Jr. et al., "Marshall-Marchetti Procedure: Modification", J. Urol., 1966, 96:737-739.
Miklos, Mini Sling Incontinence Treatment—Vagina Plastic Surgery, http://www.miklosandmoore.com/mini_sling.php, Feb. 28, 2011.
MiniArc Single-Incision Sling http://www.americanmedicalsystems.com Mar. 4, 2011.
Moir, "The Gauze-Hammock Operation," The Journal of Obstetrics and Gynaecology of the British Commonwealth, 1968, 75(1):1-9.
Monseur, J., Anatomic Chirurgicale: Les Ligaments Du Perinee Feminin, Sep. 4, 2008.
Moore et al. "Single-Center Retrospective Study of the Technique, Safety, and 12 Month Efficacy or the MiniArc™ Single Incision Sling: A New Minimally invasive Procedure for Treatment of Female SUI" [Online] 2009, 18, pp. 175-181.
Morgan et al., "The Marlex sling operation for the treatment at recurrent stress urinary incontinence: A 16-year review," Am. J. Obstet. Gynecol., 1985, 151:224-226.
Morgan, "A sling operation, using Marlex polypropylene mesh, for treatment of recurrent stress incontinence," Am. J. Obstet. Gynecol,, 1970, 106(3):369-376.
Narik and Palmrich, "A simplified sling operation suitable for routine use," Am. J. Obstet. Gynecol., 1962, 84:400-405.
Nichols, "The Mersilene Mesh Gauze-Hammock for Severe Urinary Stress Incontinence," Obstet. Gynecol., 1973, 41 (1):88-93.
Nicita, Giulio, (1998), "A New Operation for Genitourinary Prolapse," The Journal of Urology, 160:741-745.
Nickel et al., "Evaluation of a Transpelvic Sling Procedure With and Without Colpolsuspension for Treatment of Female Dogs With Refractory Urethral Sphincter Mechanism Incompetence," Veterinary Surgery, 1998, 27:94-104.
Norris et al., "Use of Synthetic Material in Sling Surgery: A Minimally Invasive Approach," J. Endocrinology, 1996, 10(3):227-230.
Novak, "Abdonomovaginal Techniques," Gynecological Surgical Technique, 1977, Piccin Editore, Padua, 5 pages.
O'Donnell, "Combined Raz Urethral Suspension and McGuire Pubovaginal Sling for Treatment of Complicated Stress Urinary Incontinence," J. Arkansas Medical Society, 1992, 88(8):389.
Order dismissing cases (Sep. 16, 2004) Civ. No. 03-5759 and Civ. No. 04-1000.
Parra and Shaker, "Experience with a Simplified Technique for the Treatment of Female Stress Urinary Incontinence," British Journal of Urology, 1990, 66:615-617.
Pelosi II and Pelosi III, "New transobturator sling reduces risk of injury," OBG Management, 2003, pp. 17-37.
Pelosi III and Pelosi, "Pubic Bone Suburethral Stabilization Sling: Laparoscopic Assessment of a Transvaginal Operation for the Treatment of Stress Urinary Incontinence," Journal of Laparoendoscopic & Advanced Surgical Techniques, 1999, 9(1):45-50.
Penson and Raz, "Why Anti-incontinence Surgery Succeeds or Fails," Female Urology, 1996, Raz (ed.), W.B. Saunders Company, Chapter 41, pp. 435-442.
Pereyra et al., "Pubourethral Supports in Perspective: Modified Pereyra Procedure for Urinary Incontinence," Obstet Gynecol., 1982, 59:643-648.
Petros and Konsky, "Anchoring the midurethra restores bladder-neck anatomy and continence," The Lancet, 1999, 354:997-998.
Petros and Ulmsten, "An analysis of rapid pad testing and the history for the diagnosis of stress incontinence," Acta Obstet. Gynecol, Scand., 1992, 71:529-536.
Petros and Ulmsten, "An Anatomical Basis for Success and Failure of Female Incontinence Surgery," Scand. J. Urol. Nephrol., 1993, (Suppl. 3):55-60.

(56) References Cited

OTHER PUBLICATIONS

Petros and Ulmsten, "An Integral Theory and Its Method for the Diagnosis and Management of Female Urinary Incontinence," 153 Scand, J. Urol. Nephrol. 1, 64 (1993).
Petros and Ulmsten, "An Integral Theory of Female Urinary Incontinence," Acta Obstet. Gynecol. Scand., 1990, 69 (Suppl.153):7-31.
Petros and Ulmsten, "Bladder Instability in Women: A Premature Activation of the Micturition Reflex," Neurourology and Urodynamics, 1993, 12:235-239.
Petros and Ulmsten, "Cough Transmission Ratio: An Indicator of Suburethral Vaginal Wall Tension Rather than Urethral Closure?" Acta Obstet. Gynecol. Scand., 1990, 69(Suppl. 153):37-38.
Petros and Ulmsten, "Cure of Stress Incontinence by Repair of External Anal Sphincter," Acta. Obstet. Gynecol Scand., 1990, 69(Suppl. 153):75.
Petros and Ulmsten, "Cure of Urge Incontinence by the Combined Intravaginal Sling and Tuck Operation," Acta Obstet. Gynecol. Scand., 1990, 69(Suppl. 153)61-62.
Petros and Ulmsten, "Further Development of the Intravaginal Slingplasty Procedure—IVS III—(with midline "tuck")," Scand. J. Urol. Nephrol., 1993, Suppl. 153:69-71.
Petros and Ulmsten, "Non Stress Non Urge Female Urinary Incontinence—Diagnosis and Cure: A Preliminary Report," Acta Obstet. Gynecol. Scand., 1990, 69(Suppl. 153):69-70.
Petros and Ulmsten, "Part I: Theoretical, Morphological, Radiographical Correlations and Clinical Perspective," Scand. J. Urol. Nephrol., 1993, Suppl. 153:5-28.
Petros and Ulmsten, "Part II:The Biomechanics of Vaginal Tissue and supporting Ligaments with Special Relevance to the Pathogenesis of Female Urinary Incontinence," Scand. J. Urol. Nephroi., 1993, Suppl. 153:29-40.
Petros and Ulmsten, "Part III: Surgical Principles Deriving from the Theory," Scand. J. Urol. Nephrol., 1993, Suppl. 153:41-52.
Petros and Ulmsten, "Part IV: Surgical Applications of the Theory—Development of the Intravaginal Sling Plasty (IVS) Procedure," Scand, J. Urol. Nephrol., 1993, Suppl. 153:53-54.
Petros and Ulmsten, "Pinch Test for Diagnosis of Stress Urinary Incontinence," Acta Obstet. Gynecol. Scand., 1990, 69(Suppl. 153):33-35.
Petros and Ulmsten, "Pregnancy Effects on the Intravaginal Sling Operation," Acta Obstet. Gynecol. Scand., 1990, 69 (Suppl.153):77-78.
Petros and Ulmsten, "The Combined Intravaginal Sling and Tuck Operation. An Ambulatory Procedure for Cure of Stress and Urge Incontinence," Acta Obstet, Gynecol. Scand., 1990, 69(Suppl. 153):53-59.
Petros and Ulmsten, "The Development of the Intravaginal Slingplasty Procedure:IVS-II—(with bilateral "tucks")," Scand. J. Urol. Nephrol., 1993, Suppl. 153:61-67.
Petros and Ulmsten, "The Free Graft Procedure for Cure of the Tethered Vagina Syndrome," Scand. J. Urol. Nephrol., 1993, Suppl. 153:85-87.
Petros and Ulmsten, "The Further Development of the Intravaginal Slingplasty Procedure: IVS IV—(with "double-breasted" unattached vaginal flap repair and "free" vaginal tapes)," Scand. J. Urol. Nephrol., 1993, Suppl. 153:73-79.
Petros and Ulmsten, "The Intravaginal Slingplasty Procedure: IVS VI—further development of the "double-breasted" vaginal flap repair—attached flap," Scand. J. Urol. Nephrol., 1993, Suppl. 153:81-84.
Petros and Ulmsten, "The Posterior Fornix Syndrome: A Multiple Symptom Complex of Pelvic Pain and Abnormal Urinary Symptoms Deriving from Laxity in the Posterior Fornix of Vagina," Scand, J. Urol. Nephrol., 1993, Suppl. 153:89-93.
Petros and Ulmsten, "The Role of a Lax Posterior Vaginal Fornix in the Causation of Stress and Urgency Symptoms: a Preliminary Report," Acta Obstet. Gynecol. Scand., 1990, 69(Suppl. 153):71-73.
Petros and Ulmsten, "The Tethered Vagina Syndrome, Post Surgical Incontinence and I-Plasty Operation for Cure," Acta Obstet. Gynecol Scand., 1990, 69(Suppl.153):83-67.
Petros and Ulmsten, "The Tuck Procedure: A Simplified Vaginal Repair for Treatment of Female Urinary Incontinence," Acta Obstet. Gynecol. Scand., 1990, 69(Suppl.153):41-42.
Petros and Ulmsten, "Urethral Pressure Increase on Effort Originates From Within the Urethra, and Continence From Musculovaginal Closure," Neurourology and Urodynamics, 1995, 14:337-350.
Petros et al., "The Autogenic Ligament Procedure: A Technique for Planned Formation of an Artificial Neo-Ligament," Acta Obstet, Gynecol. Scand., 1990, 69(Suppl. 153):43-51.
Petros, "Development of Generic Models for Ambulatory Vaginal Surgery—A Preliminary Report," Int. Urogynecol. J., 1998, 9:19-27.
Plaintiff Coloplast ,A/S's Opening Claim Construction Brief (Jan. 10, 2011) *Coloplast A/S, v. Generic Medical Devices, Inc.*, Court File No. CV 10-227 BHS.
Plaintiff Coloplast A/S's Answer to Defendant Generic Medical Devices, Inc.'s Counterclaims (Mar. 22, 2010) *Coloplast A/S,* v. *Generic Medical Devices, Inc.*, Court File No. CV10-227 BHS.
Plaintiff Coloplast A/S's Disclosure of Asserted Claims and Infringement Contentions (Jul. 6, 2010) *Coloplast A/S,* v. *Generic Medical Devices, Inc.*, Court File No. CV '10-227 BHS.
Plaintiff's Reply to Counterclaim (Mar. 30, 2004) *Mentor Corporation* v. *American Medical Systems, Inc.* (Civ. No. 04-1000).
Product Monograph for Aris Transobturator Tape for the Treatment of Female Stress Urinary Incontinence, 2004, 40 pages.
Rackley et al., "Tension-free Vaginal Tape and Percutaneous Vaginal Tape Sling Procedures," Techniques in Urology, 2001, 7(2):90-100.
Rackley, "Synthetic slings: Five steps for successful placement—Follow these steps to insert Transvaginal/Percutaneous slings using vaginal approach alone," Urology Times, 2000, 28:46-49.
Raz et al., "Urological Neurology and Urodynamics," J. Urol., 1992. 148:845-850.
Raz, "Modified Bladder Neck Suspension for Female Stress Incontinence," Urology, 1981, 17(1):82-85.
Richardson et al., "Delayed Reaction to the Dacron Buttress Used in Urethropexy," J. Reproductive Med., 1984, 29 (9):689-692.
Ridley, "Appraisal of the Goebell-Frandenheim-Stoeckel sling procedure," Am. J. Obstet. Gynecol., 1966, 95(5):714-721.
Schumpelick, V. et at,, "Minimized polypropylene mesh for preperitoneal net plasty (PNP) of incisional hernias," Chirurg 70:422-430 (1999).
Shaw, W., "An Operation for the Treatment of Stress Incontinence," Br. Med. J. 1949:1070-1073.
Sheiner et al., "An unusual complication of obturator foramen arterial bypass," J. Cardiovasc. Surg., 1969, 10(4):324-328.
Siris and Leach, "Use of Fascia Late for Pubovaginal Sling," Female Urology, 1996, Raz (ed.). W.B. Saunders Company, Chapter 32, pp. 376-381.
Sloan and Barwin, "Stress Incontinence of Urine: A Retrospective Study of the Complications and Late Results of Simple Suprapubic Suburethral Fascial Slings," J. Urol., 1973, 110:533-536.
Spencer et al., "A Comparison of Fndoscopic Suspension of the Vesical Neck with Suprapubic Vesicourethropexy for Treatment of Stress Urinary Incontinence," J. Urol., 1987, 137:411-415.
Spinosa, JP et al., Transobturator surgery for female stress incontinence: a comparative anatomical study of outside-in vs. inside-out techniques, BJU Intl., 100(5), pp. 1097-1102 (Nov. 2007).
Stamey, "Endoscopic Suspension of the Vesical Neck for Urinary Incontinence in Females," Annals of Surgery, 1980, 192(4):465-471.
Stanton, "Suprapubic Approaches for Stress incontinence in Women," J. Am. Geriatrics Soc., 1990, 38(3):348-351.
Staskin et al., "The Gore-tex sling procedure for female sphincteric incontinence: indications, technique, and results," World J. Urol., 1997, 15:295-299.
Stothers et al., "Anterior Vaginal Wall Sling," Female Urology, 1996, Raz (ed.), W.B. Saunders Company, Chapter 35, pp. 395-398.
Ulmsten and Petros, "Intravaginal Slingplasty (IVS): An Ambulatory Surgical Procedure for Treatment of Female Urinary Incontinence," Scand. J. Urol. Nephrol, 1995, 29:75-82.
Ulmsten et al., "A three-year follow up of tension free vaginal tape for surgical treatment of female stress urinary incontinence," Br. J. Obstet. Gynecol., 1999, 106:345-350.

(56) References Cited

OTHER PUBLICATIONS

Ulmsten et al., "An Ambulatory Surgical Procedure Under Local Anesthesia for Treatment of Female Urinary Incontinence," Int. Urogynecol. J., 1996, 7:81-86.
Ulmsten et al., "Different Biochemical Composition of Connective Tissue in Continent and Stress Incontinent Women," Acta Obstet. Gynecol. Scand., 1987, 66:455-457.
Ulmsten et al., "The unstable female urethra," Am. J. Obstet. Gynecol., 1982, 144:93-97.
Ulmsten, "Female Urinary Incontinence—A Symptom, Not a Urodynamic Disease. Some Theoretical and Practical Aspects on the Diagnosis and Treatment of Female Urinary Incontinence," Int. Urogynecol. J., 1995, 6:2-3.
Ulstem et al., "A Multicenter Study of Tension-Free Vaginal Tape (TVT) for Surgical Treatment of Stress Urinary Incontinence," Int. Urogynecol. J., 1998, 9:210-213.
U.S. Appl. No. 13/149,994, filed Jun. 1, 2011.
U.S. Appl. No. 10/106,086, filed Mar. 25, 2002.
U.S. Appl. No. 11/199,061, filed Aug. 8, 2005.
U.S. Appl. No. 60/279,794, filed Mar. 29, 2001.
U.S. Appl. No. 60/302,929, filed Jul. 3. 2001.
U.S. Appl. No. 60/307,836, filed Jul. 25, 2001.
U.S. Appl. No. 60/322,309, filed Sep. 14, 2001.
U.S. Appl. No. 60/362,806, filed Mar. 7, 2002.
U.S. Appl. No. 60/380,797, filed May 14, 2002.
U.S. Appl. No. 60/393,969, filed Jul. 5, 2002.
U.S. Appl. No. 60/402,007, filed Aug. 8, 2002.
U.S. Appl. No. 60/414,865, filed Sep. 30, 2002.
Webster and Kreder, "Voiding Dysfunction Following Cystourethropexy: Its Evaluation and Management," J. Urol., 1990. 144:670-673.
Weidemann, Small Intestinal Submucosa for Pubourethral Sling Suspension for the Treatment of Stress Incontinence: First Histopathological Results in Humans, Jul. 2004.
Winter, "Peripubic Urethropexy for Urinary Stress Incontinence in Women," Urology, 1982, 20(4):408-411.
Woodside and Borden, "Suprapubic Endoscopic Vesical Neck Suspension for the Management of Urinary Incontinence in Myelodysplastic Girls," J. Urol., 1986, 135:97-99.
Written Opinion for PCT/GB2009/050174, dated Jun. 24, 2009.
Written Opionion issued in PCT/GB2007/002589, dated Jan. 22, 2008, 5 pages.
Zacharin and Hamilton, "Pulsion Enterocele: Long-Term Results of an Abdominoperineal Technique," Obstet. Gynecol., 1980, 55(2)141-148.
Zacharin, "The suspensory mechanism of the female urethra," J. Anat., 1963, 97(3):423-427.

\* cited by examiner

METHOD AND DEVICE FOR TREATING URINARY INCONTINENCE

CROSS-REFERENCE TO RELATED APPLICATION

This application is a Continuation of U.S. patent application Ser. No. 13/326,334, filed on Dec. 15, 2011, which is a Continuation of U.S. patent application Ser. No. 12/547,499, filed on Aug. 26, 2009 and now issued as U.S. Pat. No. 8,469,875, which is a Continuation of U.S. patent application Ser. No. 11/040,698, filed on Jan. 21, 2005 and now issued as U.S. Pat. No. 7,621,864, which is a Continuation of U.S. patent application Ser. No. 10/455,465, filed on Jun. 4, 2003, now abandoned, which is a Divisional of U.S. patent application Ser. No. 10/092,069, filed Mar. 5, 2002, and now issued as U.S. Pat. No. 6,638,211, which is a Continuation of PCT/FR01/02120, filed on Jul. 3, 2001, designating the United States and published in French as WO 02/02031 on Jan. 10, 2002, which claims priority from French Patent Application Serial No. 00/08706, filed on Jul. 5, 2000. Priority to each of the foregoing is claimed.

The invention relates to a method for treating urinary incontinence in women. It also relates to an implantable device intended to correct urinary incontinence in women. The said device is more particularly suited to the treatment of stress urinary incontinence.

Various types of device have been proposed for treating phenomena of urinary incontinence in women.

Thus, for example, document U.S. Pat. No. 5,899,909 describes a tape of constant width, made of a material of the meshed or knitted polypropylene type ensuring fibroblast colonization and thus anchorage into the tissues along its entire length. Once an incision has been made in the wall of the vagina this tape is positioned under the urethra, the tape being led upwards on each side of the bladder to be anchored into the abdominal wall.

The method of fitting this tape is relatively tricky. Specifically, the needles being led vertically up alongside the bladder may not only pierce the latter, but may above all pierce the iliac artery or even the small intestine. In consequence, it is essential that cystoscopy be performed during the intervention.

Document WO 98/35632 describes a device in the form of a tape, the central region of which is wider than the body of the tape, the assembly being made of a biocompatible material, particularly a woven material, flowing for fibroblast colonization.

As before, each of the ends of the tape is led up alongside the bladder to be secured at the abdominal wall or, more specifically, in the bone of the pubis. Thus, the same drawbacks as before may be encountered.

One of the objects of the invention is to artificially reconstruct the pelvic fascia by fitting tapes aimed at restoring, as faithfully as possible, the effective and natural situation of the endo-pelvic fascia, in its role of fibrous plug obturating the uro-genital opening, the said fascia resting on either side of the said opening on the floor of the lifting muscles.

Another of the stated objects of the present invention lies in solving the problems associated with subsequent surgical re-intervention in the region of the urethra; given the fact that the tapes proposed by the Prior Art are made, along their entire length, of a material capable of being colonized by fibroblasts, the problem arises of performing an intervention in this region if the tape, because of the fibroblast colonization, is anchored to the periurethral wall. A solution to this new problem is all the more important now that it has been found that the phenomenon of urinary incontinence may evolve to the fitting of an artificial sphincter. A problem such as this is neither disclosed nor suggested in the Prior Art.

Furthermore, the literature has described possible phenomena of the migration of the substance of which the tape is made, particularly polypropylene, into the viscera.

In order to solve all of these problems, the Applicant is proposing a method and an implantable device, intended to correct urinary incontinence in women.

This method for treating urinary incontinence in women comprises the following steps:

making a mediane paraurethral incision, practically in the middle third of the urethra, measured from the meatus, so as to allow the passage of a tape between the Alban fascia and the periurethral fascias;

extending each of the free ends of the said tape in the region of the two obturator foramen of the iliac wing and leading them out into the groin opposite the corresponding foramen so that they essentially form a V shape, the point of which V passes under the urethra without changing the position thereof.

In other words, and contrary to the surgical techniques employed in the state of the art, the tape is not led up alongside the bladder to form a U and thus be situated in close proximity to vital organs, but is on the contrary diverted from the bladder to form a V. Hence, no risk of damaging the bladder, the iliac artery or the small intestine is run. In consequence, it is not necessary to perform cystoscopy during the intervention.

According to the invention, in order to make it easier to fit the tape which acts as an implant, a space is made between, on the one hand, the Alban fascia, the perineal muscular plane and the anterior insertion of the puborectal muscle and, on the other hand, the periurethral fascias.

According to an advantageous version of the invention, the central region of the tape or implant, which region is intended to be inserted between the Alban fascia and the periurethral fascias, is coated with a substance capable of preventing any adhesion of the said fascias to the tape.

Thus it becomes possible to avoid any cell growth on the tape between the wall of the vagina and the wall of the urethra, hence avoiding any anchorage of the tape in this region and thus to allow subsequent surgical re-intervention. Furthermore, coating it with such a substance in the region of the urethra makes it possible to avoid any migration of polypropylene into the viscera.

The device according to the invention is characterized in that it is in the form of a tape of which the central region, intended to be inserted between the Alban fascia and the periurethral fascia, is coated with a substance capable of preventing any adhesion of the said fascias to the tape.

In a first embodiment, the substance that prevents adhesion of the fascias to the tape is silicone.

In a second embodiment, the substance is made of vegetable or animal growth factors.

Of course, any substance capable of avoiding the adhesion of the fascias to the tape may be envisaged.

The tape is coated on both side, advantageously on one side.

Furthermore, the tape is made of any materials such as those known to those skilled in the art and, in particular but without applying any limitation, any material chosen from the group containing polyethylene and polypropylene.

According to another feature, when the tape is made of polypropylene, the polypropylene is either meshed or knitted or alternatively is in the form of sprayed fibres. Nevertheless, the tape can also be made of absorbable material.

In one advantageous embodiment, the central region of the tape is not as wide as the rest of the tape and this is so as to limit the area of contact in the region of the Alban fascia and of the periurethral fascia.

Furthermore, and according to another feature, each of the ends of the tape has a tapered point intended to be anchored in the groin facing the corresponding obturator foramen.

According to a preferred embodiment, the tape has a length equal to 60 cm and a width equal to 2.5 cm, and has a central region which is not as wide, being 1 cm wide over a length equal to 3 cm. Advantageously, the central region has a length equal to 15 mm.

The invention and its ensuing advantages will emerge better from the following example in support of the appended figures.

Figure 1:
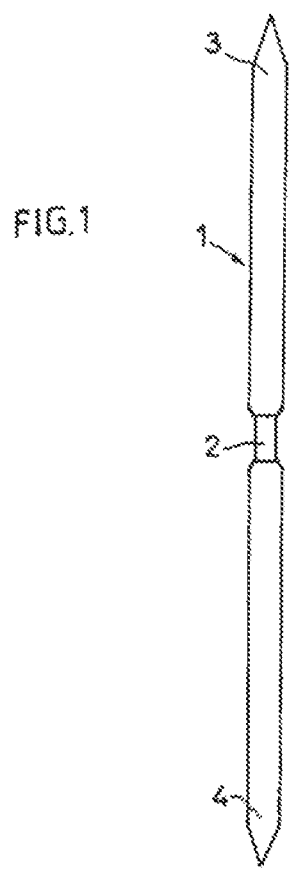
FIG. 1 is a diagrammatic depiction of the tape of the invention.

As shown in FIG. 1, the device of the invention is in the form of a tape (1) of a length equal to 60 cm and of a width equal to 2.5 cm. This tape is made, along its entire length, of sprayed polypropylene fibres.

According to an advantageous feature, the tape has, at its centre (2), a narrowing of length equal to 3 cm and of width equal to 1 cm, this portion being coated on both sides with a silicone-containing substance. Furthermore, each of its free ends (3, 4) is tapered.

Fitting the device requires mini-invasive surgery, the main steps of which are described hereinafter.

First of all, a mediane paraurethral incision is made in the region of the middle third of the urethra.

One of the two obturator foramen, and more specifically the lower internal part is then identified by a finger slipped into the vaginal incision and an incision is made in the perineal skin opposite it, and so in the groin, so as to form an orifice through which an Emmet needle is then passed. This needle is introduced through this cutaneous incision firstly perpendicular to the perineum for about 15 mm (passing through the internal obturator muscle as far as just outside the ischiopubic branch), then the needle is allowed to describe its curvature, guided in this by the finger introduced opposite the obturator muscle through the vaginal incision. The pointed end of the tape is then slipped into the eye of the needle, emerging from the said vaginal incision, then pulled back through the thickness of muscle, the retractor and the internal obturator up to the surface of the skin.

The tape is then placed between the Alban fascia and the periurethral fascias to position it in such a way that its central region, coated with silicone as appropriate, faces the said fascias. The tape is positioned without pulling behind the urethra.

An incision is then made in the perineal skin facing the second obturator foramen, into which incision an Emmet needle is inserted. The free end of the tape is then slipped into the eye of the needle which is pulled back in the same way as before.

The excess tape is then cut off flush with the skin then the skin is immobilized to disconnect it from the tape. The incision is finally closed with a stitch of quickly absorbable suture.

Figure 2:
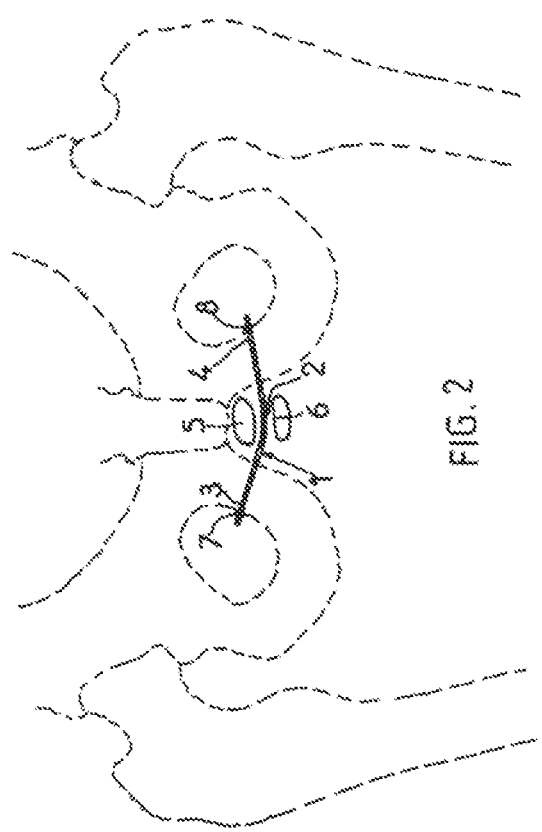
FIG. 2 is a diagrammatic depiction of the position of the tape after fitting.

FIG. 2 diagrammatically depicts the position, in cross section, of the tape after it has been fitted. As shown in this figure, once in place, the tape adopts the shape of a V, the branches of which are very far apart.

Furthermore, it can also be seen that when the tape according to one of the advantageous embodiments of the invention is used, the silicone-coated segment of the tape is positioned between the uterus (5) and the vagina (6), while its ends (3, 4) are secured in the region of the groin (7, 8) facing the obturator foramen.

Thanks to the robustness and texture of the tape, tension can be strong without there being any risk of rupture. The tape is positioned under the control of sight without employing cystoscopy. It is essential that there be no pulling on this tape which has to be slipped down under the urethra without altering the position thereof.

It is apparent from the foregoing that the method according to the invention for treating urinary incontinence in women differs from the methods proposed in the state of the art through the simplicity of fitting of the tape, using mini-invasive surgery. Furthermore, it provides the urethra with firm suspension while at the same time maintaining a certain degree of flexibility and, most of all, keeping the vital organs in the vicinity relatively far away from the said tape. Furthermore, it plays a part in reconstructing the endopelvic fascia.

What is claimed is:

1. A method for treating urinary incontinence, the method comprising:
   making a vaginal incision in a patient creating a uro-genital opening;
   inserting an implant into the patient through the vaginal incision, the implant comprising a central region, a tapered first end region that is tapered to a first end, and a tapered second end region that is tapered to a second end;
   positioning the central region of the implant under a urethra of the patient, the urethra having a first side and a second side, the first and second sides being defined on opposing sides of a medial plane of the urethra; and
   obturating the uro-genital opening and restoring endopelvic fascia through positioning the implant by directing the tapered first end region of the implant through the vaginal incision away from the medial plane and the first side of the urethra of the patient and toward a first groin area, and directing the tapered second end region of the implant through the vaginal incision away from the medial plane and the second side of the urethra of the patient and toward a second groin area.

2. The method for treating urinary incontinence of claim 1, wherein positioning the central region and the first and second ends of the implant includes the implant defining a V-shape.

3. The method for treating urinary incontinence of claim 1, wherein the first and second end regions of the implant terminate subcutaneously.

4. The method for treating urinary incontinence of claim 1, further comprising utilizing a curved needle to divert each of the tapered first end region and the tapered second end region away from a bladder of the patient.

5. The method for treating urinary incontinence of claim 4, further comprising inserting a finger into the incision and guiding the curved needle such that the curved needle follows a curved path through the patient's pelvic tissue.

6. The method for treating urinary incontinence of claim 4, further comprising attaching the tapered first end region of the implant to the curved needle and utilizing the curved needle to divert the first end of the implant away from the bladder of the patient, and attaching the tapered second end region of the implant to the curved needle and utilizing the curved needle to divert the second end region of the implant away from the bladder of the patient.

7. The method for treating urinary incontinence of claim 1, further comprising utilizing a curved Emmet needle to divert each of the tapered first end region and the tapered second end region away from a bladder of the patient.

8. The method for treating urinary incontinence of claim 1, wherein the implant is in the form of a surgical tape and inserting the implant into the patient through the vaginal incision comprises inserting the surgical tape into the patient through the vaginal incision.

9. The method for treating urinary incontinence of claim 1, wherein the implant is in the form of one of a polyethylene tape material and a polypropylene tape and inserting the implant into the patient through the vaginal incision comprises inserting one of the polyethylene tape material and the polypropylene tape material into the patient through the vaginal incision.

10. The method for treating urinary incontinence of claim 1, wherein the implant is in the form of one of a mesh implant, a knitted implant, and a sprayed fiber implant and inserting the implant into the patient through the vaginal incision comprises inserting one of the mesh implant, the knitted implant, and the sprayed fiber implant into the patient through the vaginal incision.

11. The method for treating urinary incontinence of claim 1, wherein the central region of the implant is coated with an adhesion preventing material and inserting the implant into the patient through the vaginal incision comprises inserting the implant having the central region coated with the adhesion preventing material into the patient through the vaginal incision.

12. The method for treating urinary incontinence of claim 1, wherein the central region of the implant is coated with silicone and inserting the implant into the patient through the vaginal incision comprises inserting the implant having the central region coated with silicone into the patient through the vaginal incision.

13. The method for treating urinary incontinence of claim 1, wherein a length of excess tape including the tapered first end region of the implant extends externally to the patient through the skin of the patient following insertion of the implant into the patient, the method further comprising removing the length of excess tape.

14. The method for treating urinary incontinence of claim 13, wherein removing the length of excess tape comprises cutting the tape flush with a skin surface of the patient.

15. The method for treating urinary incontinence of claim 14, further comprising disconnecting any portion of the tape attached to the skin surface of the patient, immobilizing the skin surface of the patient, and closing any associated incision in the skin surface of the patient.

16. The method for treating urinary incontinence of claim 1, wherein positioning the first end region and the second end region of the implant does not alter a position of the urethra.

17. The method for treating urinary incontinence of claim 1, wherein the central region has a first width and each of the tapered first and second end regions has a width different than the first width, and wherein inserting the implant into the patient through the vaginal incision comprises inserting the implant having the central region with the first width and the tapered first and second end regions having widths different than the first width into the patient through the vaginal incision.

18. A method for treating urinary incontinence, the method comprising:
   making a vaginal incision in a patient and forming a uro-genital opening;
   inserting an implant into the patient through the vaginal incision, the implant comprising a central region, a first end region, and a second end region;
   inserting a finger into the incision and guiding a curved needle along a curved path through pelvic tissue of the patient;
   diverting a tapered portion of the first end region of the implant away from a medial plane of the urethra and laterally away from a bladder of the patient with the curved needle;
   diverting a tapered portion of the second end region of the implant laterally away from the bladder of the patient;
   positioning a center of the central region of the implant under the urethra of the patient thereby restoring endopelvic fascia by obturating the uro-genital opening with the implant; and
   removing the curved needle from the implant.

* * * * *